(12) United States Patent
Lauraeus et al.

(10) Patent No.: US 9,975,062 B2
(45) Date of Patent: May 22, 2018

(54) NANOFIBRILLAR CELLULOSE AS A PHASE SEPARATION AGENT

(71) Applicant: UPM-KYMMENE CORPORATION, Helsinki (FI)

(72) Inventors: Marko Lauraeus, Vihti (FI); Antti Laukkanen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 829 days.

(21) Appl. No.: 14/368,013

(22) PCT Filed: Dec. 18, 2012

(86) PCT No.: PCT/FI2012/051265
§ 371 (c)(1),
(2) Date: Jun. 23, 2014

(87) PCT Pub. No.: WO2013/093198
PCT Pub. Date: Jun. 27, 2013

(65) Prior Publication Data
US 2014/0378676 A1    Dec. 25, 2014

(30) Foreign Application Priority Data

Dec. 22, 2011  (FI) .................................. 20116315

(51) Int. Cl.
*B01D 21/01*    (2006.01)
*C02F 1/52*     (2006.01)
(Continued)

(52) U.S. Cl.
CPC ......... *B01D 15/02* (2013.01); *B01D 17/0202* (2013.01); *B01D 17/047* (2013.01);
(Continued)

(58) Field of Classification Search
None
See application file for complete search history.

(56) References Cited

U.S. PATENT DOCUMENTS 5,106,966 A    4/1992   Thomas et al.
5,175,271 A    12/1992  Thomas et al.
(Continued)

FOREIGN PATENT DOCUMENTS

EP    0418517 A2    3/1991
EP    2236545 A1    10/2010
(Continued)

OTHER PUBLICATIONS

Cervin et al. ("Ultra porous nanocellulose aerogels as separation medium for mixtures of oil/water liquids", Cellulose, published online Dec. 17, 2011, 19, 401-410).*
(Continued)

*Primary Examiner* — Clare M Perrin
(74) *Attorney, Agent, or Firm* — Nixon Peabody LLP (57) ABSTRACT

Disclosed is the use of a separation agent including fibril cellulose for phase separation, as well as to a method for the separation of at least one liquid phase from at least one phase selected from a second liquid phase, solid phase and semi-solid phase, where the method includes the steps of incorporating a separation agent including fibril cellulose to a mixture where separation of the phases is desired, followed by formation of phases and removing the phases.

7 Claims, 3 Drawing Sheets

(51) Int. Cl.
| | |
|---|---|
| B01D 15/02 | (2006.01) |
| C08B 15/00 | (2006.01) |
| B01J 20/28 | (2006.01) |
| C02F 1/28 | (2006.01) |
| B01D 17/04 | (2006.01) |
| C12N 15/10 | (2006.01) |
| B01J 20/24 | (2006.01) |
| B01D 17/02 | (2006.01) |
| C02F 1/00 | (2006.01) |
| B03D 3/00 | (2006.01) |
| B01D 15/00 | (2006.01) |
| C08B 1/00 | (2006.01) |
| C02F 1/56 | (2006.01) |

(52) U.S. Cl.
CPC ............ *B01D 17/048* (2013.01); *B01J 20/24* (2013.01); *B01J 20/28023* (2013.01); *B01J 20/28047* (2013.01); *C02F 1/286* (2013.01); *C02F 1/5263* (2013.01); *C02F 1/5272* (2013.01); *C08B 15/00* (2013.01); *C12N 15/1017* (2013.01); *C02F 1/56* (2013.01); *C08J 2301/02* (2013.01); *C08J 2401/02* (2013.01)

(56) References Cited

U.S. PATENT DOCUMENTS

| | | | |
|---|---|---|---|
| 5,625,055 | A | 4/1997 | Caddy et al. |
| 2007/0092901 | A1 | 4/2007 | Ligler et al. |
| 2009/0305033 | A1* | 12/2009 | Yano .................. D21H 21/26 428/339 |
| 2014/0374254 | A1 | 12/2014 | Lauraeus et al. |

FOREIGN PATENT DOCUMENTS

| | | |
|---|---|---|
| JP | H04-295759 A | 10/1992 |
| JP | H07-232060 A | 9/1995 |
| JP | S63-304001 A | 12/1998 |
| JP | 2005-172773 A | 6/2005 |
| JP | 2009-051797 A | 3/2009 |
| JP | 2011-80171 A | 4/2011 |
| JP | 2015-507181 A | 3/2015 |
| WO | 2011079380 A1 | 7/2011 |
| WO | 2012107642 A1 | 8/2012 |

OTHER PUBLICATIONS

Korhonen et al. ("Hydrophobic Nanocellulose Aerogels as Floating, Sustainable, Reusable, and Recyclable Oil Adsorbents", Applied Materials and Interfaces, published May 31, 2011, 3, 1813-1816).*
Appaw et al., "Phase separation and heat-induced gelation characteristics of cellulose acetate in a mixed solvent system", Cellulose, 2010, vol. 17, pp. 533-538.
Cervin et al., "Ultra porous nanocellulose aerogels as separation medium for mixtures of oil/water liquids", Cellulose, 2012, vol. 19, pp. 401-410.
Tabuchi et al., "Bio-sensing on a chip with compact discs and nanofibers", Lab Chip, 2005, vol. 5, pp. 1412-1415.
Tabuchi et al., "Design for DNA Separation Medium Using Bacterial Cellulose Fibrils", Anal. Chem., 2005, vol. 77, pp. 7090-7093.
Xhanari et al., "Emulsions Stabilized by Microfibrillated Cellulose: The Effect of Hydrophobization, Concentration and O/W Ratio", Journal of Dispersion Science and Technology, 2011, vol. 32, pp. 447-452.
International Search Report, dated Mar. 27, 2013, from corresponding PCT application.
Office Action in Japanese Patent Invention No. 2014-548120, dated Feb. 17, 2017 (5 pages).
Japanese Patent Office, Decision of Refusal in co-pending Application No. 548120/2014, dated Sep. 5, 2017, with English translation (7 pages).

* cited by examiner

NANOFIBRILLAR CELLULOSE AS A PHASE SEPARATION AGENT

FIELD OF THE INVENTION

The invention relates to new applications of fibril cellulose. Particularly the invention relates to the use of fibril cellulose as a separation agent for interphase separation, as well as for the separation of solid materials from liquid phase. The invention also relates to a phase lock or phase separation agent comprising fibril cellulose. Further, the invention relates to a method for the separation of liquid phases and solid or semi-solid compounds. The invention also relates to a kit or device comprising said separation agent.

BACKGROUND

Many methods and processes in the field of life sciences, molecular biology, process chemistry and organic chemistry comprise one or more steps, typically separation or extraction steps where two or more phases, such as organic (non-aqueous) and aqueous phase, or hydrophilic and hydrophobic phase, are required to be separated. It is also often desirable to separate solid or semi-solid materials, such as particles or aggregates from a suspension or mixture to obtain a clear liquid or a liquid containing a desired compound or compounds dissolved therein, which may be isolated from said liquid.

In molecular biology, extraction procedures are typically associated to DNA purification methods. It is often important to obtain pure samples of plasmids, nuclear DNA and RNA from samples, in assaying for genes which express particular proteins, to determine whether or not a particular sample of cell has been transfected by a foreign gene and so forth. A widely used method for extracting DNA involves differentiated solvation of the DNA and the non-DNA material, using phenol and chloroform. The DNA containing sample, typically after several preparative steps, is mixed with an organic solvent, usually phenol or a mixture of phenol and chloroform. Proteins denaturate and enter the organic phase (phenol) or precipitate at the interphase between the organic phase and aqueous phase. The aqueous phase contains the DNA. Mixing of the aqueous phase with alcohol results in the precipitation of the DNA, which then can be spooled. Standard protocols for the separation of the phases require aspiration of the aqueous DNA containing solvent. However, both solvents phenol and chloroform are regarded as potentially carcinogenic compounds. Pouring of the material from the second solvent is not acceptable because the barrier between phenol and chloroform is not very stable and contamination of phases is inevitable. At the interphase between the layers, it often becomes difficult to separate the DNA. Frequently poor phase separation and cloudy interphase between the two phases is noticed, which typically encumbers the removal of the desired phase.

Some phase lock agents have been proposed for preventing protein interphase contamination, for easing the phase separation and forming a clearer interphase between the two phase layers.

U.S. Pat. No. 5,106,966 suggests the use of a polyester gel polymer for easing phase separation and purification of DNA from a biological sample.

U.S. Pat. No. 5,175,271 relates to the use of gels based on silica gel polymers for the same purpose as above.

There is a need for new, rapid and efficient separation agent and phase lock materials to be used particularly for phase separation and for separation of solid material from liquid, suitable for applications in molecular biology, process chemistry, life sciences and organic chemistry.

SUMMARY

The invention is directed to the use and to a method of use of a separation agent comprising fibril cellulose for phase separation. Phase separation or interphase separation may comprise any of the following separations, where a first liquid phase is separated from at least one liquid phase immiscible in said first liquid phase: separation of hydrophilic and hydrophobic phases, separation of organic and inorganic phases, separation of phases having different gravity, and separation of solid or semi-solid material from liquid materials, in applications in the field of molecular biology, process chemistry, life sciences and organic chemistry.

The invention is further directed to a method for phase separation, where a first liquid phase is separated from at least one phase selected from a second liquid phase immiscible in said first liquid phase, solid phase and semi-solid phase, where the method comprises the steps of incorporating a separation agent comprising fibril cellulose to a mixture where separation of the phases is desired, followed by formation of phases and removing the phases.

In the method a separation agent comprising fibril cellulose is brought into contact with a mixture comprising at least one liquid phase and at least one component insoluble and/or immiscible in said liquid phase, followed by at least one of the steps selected from agitation, centrifugation, and then the separating the phases. Suitably the component is a liquid.

The invention is further directed to a method for the separation of nucleic acid(s) from a sample containing it, where the sample is brought into contact with at least one organic solvent and a separation agent comprising fibril cellulose, followed by forming and separation of phases.

Still further, the invention is directed to a kit for use in nucleic acid separation, comprising least one separation agent comprising fibril cellulose.

Still further, the invention is directed to a device for use in nucleic acid separation, comprising least one separation agent comprising fibril cellulose.

Further aspects of the invention are directed to a method for the prevention of interphase contamination of molecules in phase separation where a separation agent comprising fibril cellulose is incorporated to the mixture where phase separation is desired.

The characteristic features of the invention are presented in the appended claims.

DEFINITIONS

Unless otherwise specified, the terms, which are used in the specification and claims, have the meanings commonly used in the filed of life sciences, molecular biology, process chemistry and organic chemistry. Specifically, the following terms have the meanings indicated below.

The term "separation agent" refers here to an agent, which effects and/or enhances the separation of phases, where a first liquid phase is separated from at least another phase immiscible in said first liquid phase, such as hydrophilic phase and hydrophobic phase, organic phase (non-aqueous) and inorganic phase, phases with different gravities, and also the separation of liquid phase and one or more components which may be solid, semi-solid, immiscible or insoluble in said liquid phase, from each other. Said separation agent may acts as a barrier between liquid phases and form an interphase between the separated phases. Particularly in the field of molecular biology a separation agent may also be called as "phase lock agent" or "phase divider".

In the broadest sense the expression "phase separation" refers here to the separation of at least one liquid phase from other phases. Thus phase separation refers to the separation of at least two phases and particularly to the separation of at least one first liquid phase from at least another phase selected from a second liquid phase, solid phase and semi-solid phase. Particularly "phase separation" is understood here to mean separation of hydrophilic and hydrophobic phases, separation of organic and inorganic phases, separation of phases having different gravity, and separation of solid or semi-solid material from liquid materials, in applications in the field of molecular biology, process chemistry, life sciences and organic chemistry.

The expression "liquid phase" refers to suspensions, emulsions, solutions and any compounds or mixtures in liquid form.

Interphase is a phase, which is formed between the phases which are separated. It is formed of the separation agent and water and optionally solid or semi-solid material contained in the mixture where separation is desired.

The expression "aqueous phase" refers here to a phase, which contains water.

The expression "organic phase" refers here to a phase, which contains one or more non-aqueous organic solvents or organic compounds, suitably in liquid form.

As used herein, the term "fibril cellulose" is understood to encompass all microfibrillated celluloses (MFC) and nanocelluloses. Further, there are several other widely used synonyms for fibril cellulose. For example: cellulose nanofiber, nanofibrillated cellulose (CNF), nanofibrillar cellulose (NFC), nano-scale fibrillated cellulose, microfibrillar cellulose, or cellulose microfibrils.

In addition, fibril cellulose produced by certain microbes has also various synonymes, for example: bacterial cellulose (BC), microbial cellulose (MC), biocellulose, nata de coco (NDC), or coco de nata (CDN).

DETAILED DESCRIPTION OF THE INVENTION

The aim of the invention was to provide a separation agent for phase separation, particularly for applications in the field of molecular biology, process chemistry, life sciences and organic chemistry, where the separation agent aids and enhances the desired separation.

Molecular biology applications refer here for example to the separation of plasmids and nucleic acids (DNA and RNA) from samples, particularly to extracting DNA from non-DNA material, as well as to generally DNA separation methods, such as non-organic salting out where the protein components are trapped within the separation agent, typically in the form of a gel, allowing decanting of the aqueous DNA containing phase without contamination.

Process chemistry applications encompass for example extraction and separation methods, particularly the separation of semisolid or solid materials from liquid mixtures and suspensions, and also enhancing the separation of phases. Said applications include also fermentation processes.

Applications in organic chemistry particularly comprise for example the separation of aqueous and organic non-aqueous phases from each other, as well as the separation hydrophilic and hydrophobic phases from each other, and the separation of semisolid or solid materials from liquid mixtures and suspensions, and also enhancing the separation of phases.

It was surprisingly found that a separation agent comprising fibril cellulose provides an excellent means for phase separation, particularly in processes and methods in the field of molecular biology, process chemistry, life sciences and organic chemistry. The separation agent comprising fibril cellulose forms a gel in the presence of water. When said separation agent is brought into contact with a mixture comprising at least one liquid, followed by separation of phases, it forms a gel-like barrier or interphase between the phases. The formed phases are organized into layers according to their specific gravities. This means that the mixture is fractionated into separate phases according to their specific gravities. When the mixture comprises solid or semi-solid particles the gel acts as a web which traps the particles within it and said particles can then be recovered from the interphase gel.

Fibril cellulose acts efficiently as a separation agent, separation enhancer and as a phase lock agent, it forms readily a sufficiently stable and uniform barrier and provides a clear and sharp interphase between the layers.

Fibril cellulose is suitably incorporated in a mixture as an aqueous gel, or as a dry powder, which forms a gel when it is brought into contact with water or an aqueous polar solvent. A gel may also be formed of fibril cellulose and a polar solvent. Said polar solvent may be selected from lower alkyl alcohols (C1-C8), suitably methanol, ethanol, isopropanol. Suitably water is used.

Fibril cellulose is obtained from any non-animal based cellulose raw material.

The term "cellulose raw material" refers to any cellulose raw material source that can be used in production of cellulose pulp, refined pulp, and fibril cellulose.

The cellulose raw material may be based on any plant material that contains cellulose or any microbial cellulose.

Plant material may be wood and said wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed.

The cellulose raw material may be also derived from the cellulose-producing micro-organism, such as from bacterial fermentation processes. The micro-organisms can be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*.

The term "cellulose pulp" refers to cellulose fibers, which are isolated from any cellulose raw material using chemical, mechanical, thermo-mechanical, or chemi-thermo-mechanical pulping processes. Cellulose pulp, which can be pulp of plant origin, especially wood (softwood or hardwood pulp, for example bleached birch pulp) and where the cellulose molecules are oxidized in one of the above-described methods, is easy to disintegrate to fibril cellulose.

The term "fibril cellulose" refers to a collection of isolated cellulose microfibrils (nanofibers) or microfibril bundles derived from cellulose raw material. Microfibrils have typically high aspect ratio: the length exceeds one micrometer while the number-average diameter is typically below 1000 nm, preferably 1-200 nm. The diameter of microfibril bundles can also be larger but generally less than 1 μm. The smallest microfibrils are similar to so called elementary fibrils, which are typically 2-12 nm in diameter. The dimensions of the fibrils or fibril bundles are dependent on raw material and disintegration method.

Fibril cellulose is characterized by very high water retention values, a high degree of chemical accessibility and the ability to form stable gels in water and other polar solvents. Fibril cellulose product is typically a dense network of highly fibrillated celluloses. The fibril cellulose may also contain some hemicelluloses; the amount is dependent on the plant source.

To obtain fibril cellulose mechanical disintegration of cellulose pulp, oxidized cellulose raw material or microbial cellulose is carried out with suitable equipment such as a refiner, grinder, homogenizer, colloider, friction grinder, ultrasound-sonicator, fluidizer such as microfluidizer, macrofluidizer or fluidizer-type homogenizer. Preferably mechanically disintegrated fibril cellulose is used.

Several different grades of fibril celluloses have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final fibril cellulose product. Typically, non-ionic or native or neutral or non-modified grades have wider fibril diameter while the chemically modified grades are a lot thinner. Size distribution is also narrower for the modified grades.

The "fibril cellulose" refers here to one grade of fibril cellulose or a combination of two or more different grades of fibril cellulose. For example modified grades of fibril cellulose may be blended with native grade for enhancing binding of certain compounds to the gel or binding of some specific impurities etc.

The fibril cellulose may be plant derived cellulose or microbial derived cellulose or any combination thereof. Suitably plant derived native fibril cellulose is used, preferably as an aqueous gel.

Fibril cellulose is understood to encompass here also any chemically or physically modified derivates of cellulose, cellulose nanofibers or nanofiber bundles. The chemical modification may be based for example on carboxymethylation, oxidation, (TEMPO-oxidation), esterification, or etherification reaction of cellulose molecules. Anionic and cationic grades are examples of chemically modified grades. Modification may also be realized by physical adsorption of anionic, cationic, or non-ionic substances or any combination of these on cellulose surface. The described modification can be carried out before, after, or during the production of cellulose nanofibers. Modified grades are typically prepared from bleached pulps. In the modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

Chemically modified grades, such as anionic and cationic grades typically have their surface charge modified and they may suitably be used as dry powder or an aqueous gel, which is added to a mixture where separation is desired. Chemically modified grades may be used particularly in the separation of compounds, where a specific surface charge enhances the separation. Thus suitable fibril cellulose or a combination of different fibril celluloses may de selected and designed for this purpose according to the type of the compounds to be separated.

Dry powders of fibril cellulose may conveniently be manufactured by spray drying and/or lyophilization of suspension or dispersions containing said fibril cellulose, using any conventional methods known in the art.

The fibril cellulose gel or hydrogel refers here to an aqueous dispersion of fibril cellulose. The fibril cellulose has excellent gelling ability, which means that it forms a gel already at a low consistency in an aqueous medium.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where Na+ ions replace the earlier ions. The absence of any positively charged ions having a charge more than +1 is particularly advantageous in life science and molecular biology applications where complex formation of DNA with ions with charges more than +1 can be avoided. The pretreatment provides the final product excellent gelling properties and transparency. The fibril cellulose obtained from pretreated cellulose raw material is referred to here as ion exchanged fibril cellulose. According to one embodiment of the invention ion exchanged native fibril cellulose is suitably used.

Microbial purity of fibril cellulose is often essential. Therefore, fibril cellulose may be sterilized prior to use, suitably in a gel form. In addition, it is important to minimize the microbial contamination of the product before and during the mechanical disintegration, such as fibrillation. Prior to fibrillation/mechanical disintegration, it is advantageous to aseptically collect the cellulose pulp from the pulp mill immediately after bleaching stage when the pulp is still sterile.

Fibril cellulose hydrogels have typically remarkable high yield stress and high zero-shear viscosity at low concentrations. Thus, i.e. if gas bubbles are generated in the fibril cellulose hydrogels they may stay still for long periods of time. The buoyancy of gas bubbles can be, however, easily increased by lowering gas pressure (e.g. 15 mmHg) above the gel, which lowers the solubility of gas in the hydrogels phase and, respectively increases the volumes of initial gas bubbles. The increased gas bubbles escape easily to upper gas phase.

The separation agent may comprise from 0.05 to 100 wt % of fibril cellulose. Thus a separation agent comprising 100 wt % of fibril cellulose particularly refers to the use of fibril cellulose as dry powder.

The separation agent may comprise from 0.05 to 20 wt % of fibril cellulose in an aqueous dispersion, suitably from 0.1 to 5 wt %, particularly from 0.1 to 3 wt %. The water used may be tap water, deionized water, sterilized water or molecular biology grade high purity water, depending on the desired application. The aqueous dispersion may also comprise at least one polar and water miscible solvent, suitably a lower (C1-C8) alcohol, such as methanol, ethanol or isopropanol.

The separation agent may optionally comprise additives, such as coloring agents (for example congored), activated carbon, and the like, suitably in an amount 0.001-0.5 wt %.

The method for the separation of phases comprises the steps of incorporating separation agent comprising fibril cellulose to a mixture comprising the agents, components or compounds, which are separated, followed by formation of phases and removing the phases. The formation of phases comprises one or more steps selected from agitation, centrifuging and settling, depending on field and application.

In the method for the separation of a first liquid phase from at least one phase selected from a second liquid phase immiscible in said first liquid phase, solid phase and semi-solid phase, a separation agent comprising fibril cellulose, suitably in the form of dry powder or an aqueous gel, is incorporated to the mixture where separation of the phases is desired, agitated and allowed to settle whereby the phases and the interphase are formed and removing the phases The first liquid phase comprises an aqueous phase, optionally comprising at least one polar solvent.

The second liquid phase is immiscible in said first liquid phase and it may comprise organic solvents immiscible in the first liquid phase or a more hydrophobic phase than the first liquid phase.

The removing of phases may comprise one or more steps selected from decanting, pipetting, draining, pumping and any other suitable steps depending on the field and application where phase separation is desired.

The separation agent is added to the mixture where separation is desired in an amount which is sufficient to achieve a uniform layer, which can provide a barrier between phases. The layer thickness i.e. the thickness of the fibril cellulose gel is suitably at least 5 μm, suitable for providing a concentration of 1 mg of fibril cellulose/cm$^2$. Naturally the layer thickness depends on the dimensions of the equipment, particularly the vessel where the separation is carried out and volumes used in the separation, from small laboratory diagnostic scale to large industrial scale. The separation agent is aggregated at the interphase and forms a barrier between the phases.

Depending on the application it may be desirable to have stronger gels providing a tighter barrier, where the gel may be of heavier grade, having a higher viscosity, or it may be sufficient and desirable to use a gel with lighter grade having a lower viscosity. The viscosity of the gel may be adjusted by varying the concentration of the fibril cellulose in the gel and by selecting a suitable type and grade of fibril cellulose. The densities of the liquids, such as aqueous and organic, particularly the salt concentration and protein concentration of the aqueous layer have an effect on the separation. Thus the type of the separation agent may be adjusted and selected with regard to application.

Accordingly, the separation agent may be used as such and added to the mixture where separation of liquid phases is desired. The rheological properties of the fibril cellulose gel allows it to be pumped, added with a syringe etc where needed.

In small scale applications, such as in molecular biology, the separation agent (phase lock agent), suitably as a gel may be incorporated or packed in ready-to use devices, such as tubes containing the desired amount of the gel, such as from 0.5 ml to 100 ml. Alternatively, the separation agent (phase lock agent) may be incorporated or packed in syringes, containing the desired amounts of the gel, for example from 0.5 ml to 100 ml. The syringe allows self-contained dispensing into all types of containers, including tubes and micro plates.

These "ready for use" tubes and syringes can be packed, sterilized and stored, and used when desired. These rapid and simple products are ideal for small volume use.

The separation agent may also be incorporated in a kit for application in the molecular biology.

For larger scale use, phase lock agent comprising fibril cellulose may be dispersed in water at the site of use or delivered as a gel in suitable containers.

The method for the separation of nucleic acid (DNA) from a sample containing it comprises the steps where the sample in a buffer is brought into contact with at least one organic solvent and separation agent (phase lock agent) comprising fibril cellulose, followed by forming and separation of phases. Suitably the buffer is an aqueous saline buffer solution (typically acetate—NaCl) used in the art. The organic solvent is a non-aqueous organic solvent, such as phenol and chloroform or a combination thereof. The obtained mixture is added to a vessel containing the separation agent or the separation agent is added to the mixture, followed by forming and separating the phases, i.e. the aqueous phase containing the nucleic acid, the interphase comprising the fibril cellulose gel between the aqueous phase and the organic phase, and the organic phase. The forming and separation is suitably carried out by centrifuging. Additionally there may be a solid phase comprising glass beads etc. The nucleic acid containing phase may be removed by pipetting, decanting etc.

For example nucleic acid yield is increased significantly, and interphase contamination can be prevented. Also a clear improvement in the purity of the extracted DNA and RNA are due to physical separation from the interphase material. It allows easy decantation or pipetting off of the nucleic acid containing phase. Multiple extractions can be carried out in the same vessel (tube) containing the separation agent as long as maximum sample volume is not exceeded.

The separation agent present during extractions involving phenol, phenol:chloroform, and chloroform:isoamyl alcohol migrates under centrifugal force to form a seal between the organic and aqueous phase. The aqueous upper phase containing the nucleic acid material can be recovered even quantitatively by simple decantation to a fresh tube.

During centrifugation, the separation agent forms a strong barrier between the aqueous and the organic phases, sealing harmful phenol fumes beneath this barrier. The aqueous phase can then be recovered simply by decanting or pipetting. Even minute amounts of plasmid DNA, genomic DNA, DNA from gels, total DNA, Lambda DNA, and phage and M13 DNA can be recovered quickly and safely.

The separation agent is inert material and it does not interfere with standard nucleic acid restriction or modification enzymes or PCR detection or PCR based microbial enumeration. In molecular biology detection, enumeration and quantification of microbes based on techniques where real-time polymerase chain reaction (PCR) is carried out, are widely used. In PCR the microbes are broken down to release their DNA and the DNA is thereafter quantified by using specific oligonucleotide primers, thermostable DNA polymerase and appropriate thermal cycler. Typically many polymeric materials inhibit the PCR reactions and make microbial quantification unreliable. The use of the separation agent comprising fibril cellulose does not interfere with real time PCR or qPCR. It is essential that the media does not comprise materials which interfere or inhibit the PCR reactions and make microbial quantification unreliable. The separation agent comprising fibril cellulose does not interact or inhibit PCR detection or PCR based microbial enumeration as can be seen from Examples 2 and 3.

Further, the separation agent is non-toxic material and requires no special precautions when used. It provides increased protection and ease of handling when working with organic extraction mixtures.

When using the separation agent comprising fibril cellulose the phase separation is easy and cloudy or hazy interphases between the phases can be avoided. It acts as a barrier between the organic and aqueous phases. A clear interphase is formed between the phase layers. The separation agent eliminates effectively interphase contamination.

The separation agent is heat-stable and can be sterilized and used at elevated temperatures as well.

The long aspect ratio of fibril cellulose provides a firm and steady net structure of the barrier gel, and further, the gel contains no monomer residues because in the manufacture of the gel no polymerization reactions are performed.

The separation agent is suitable for various separation and extraction methods and processes in the field of molecular biology, process chemistry, life sciences and organic chemistry. It is very useful in analytics, diagnostics and it is also very valuable in methods utilized in laboratory robots. The separation agent may suitably be used in the separation of proteins, such as in the separation of proteins in blood for example in diagnostic methods, in the dairy industry, particularly in the separation of whey proteins from milk, where the separation agent in gel form traps the precipitated molecules and leaves a clear liquid for further use. In larger scale it can be used for example in fermentation processes where rapid and effective separation is needed, for example in brewing industry for the separation of yeast. The separation agent can also be used as a "liquid filter" for removing (separating) of beer yeast.

The fibril cellulose may easily be removed from the gel containing the precipitated particles, for example with enzymes using enzymatic degradation of cellulose molecules. Proper enzymes are for example commercially available cellulases. Alternatively, the gel containing separation agent and the trapped particles may be diluted with an aqueous or polar liquid; and removing the fibril cellulose by decantation. The recovered may suitably be used in animal feeds, particularly when no toxic materials are used in the method.

Yields of the separated products are increased as they are not lost in the interphase and they can be separated more efficiently.

EXAMPLES

Example 1. Fibril Cellulose as Separation Agent

Figure 1:
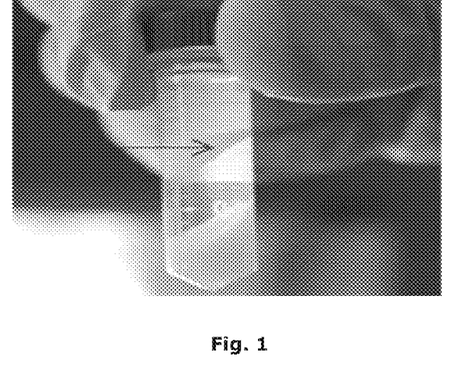
FIG. 1 is a photo of phase separation in DNA isolation using fibril cellulose as phase lock agent.
Figure 2:
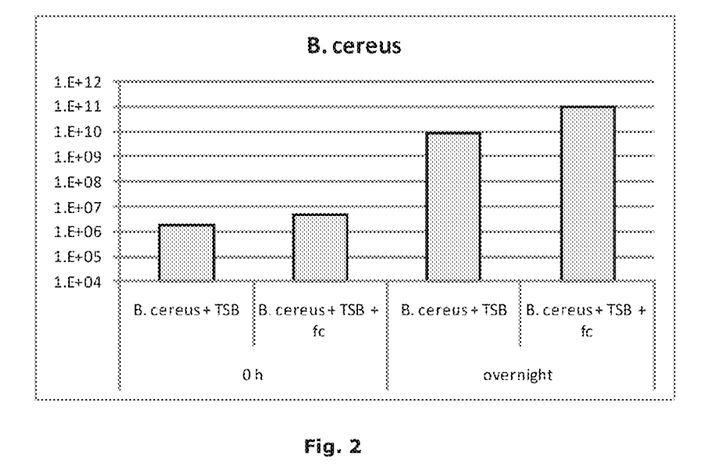
FIG. 2 illustrates graphically *B. cereus* cell numbers on growth media (TBS) and fibril cellulose (fc) in the beginning (0 h) and after overnight incubation analyzed by quantitative PCR.
Figure 3:
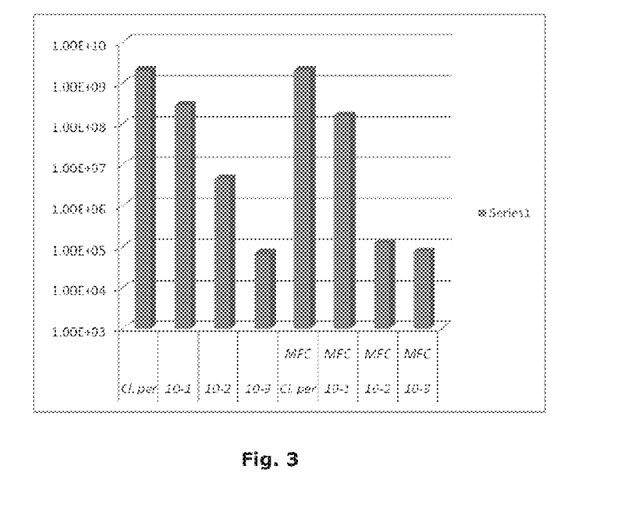
FIG. 3 illustrates graphically quantitative PCR run from *C. perfringens* dilution series that show strong linear correlation between the dilution and the PCR response in the presence or absence of 1.5% fibril cellulose.
Figure 4:
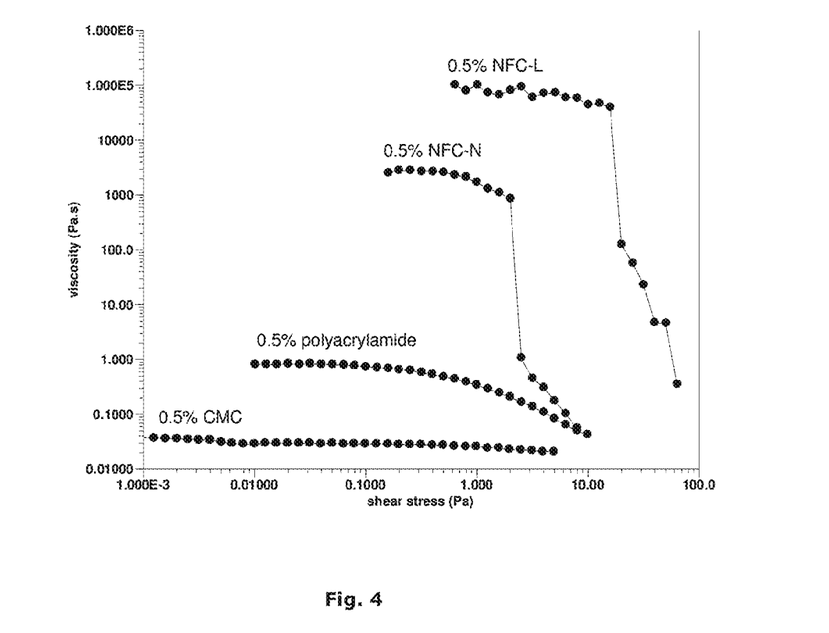
FIG. 4 shows viscosity of 0.5% fibril cellulose hydrogels as function of applied shear stress in comparison with 0.5% solution of water soluble polymers polyacrylamide (5 000 kDa) and CMC (250 kDa).
Figure 5:
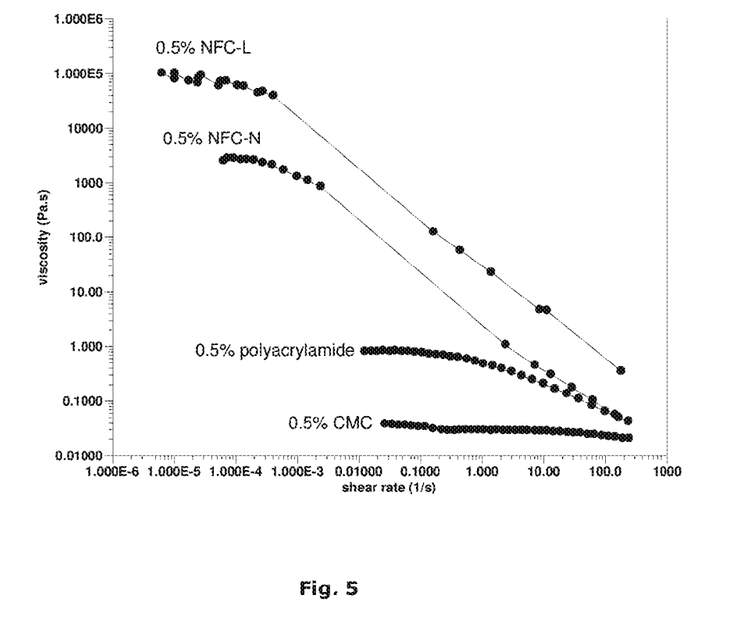
FIG. 5 depicts viscosity of 0.5% fibril cellulose hydrogels as function of measured shear rate in comparison with 0.5% polyacrylamide and CMC. Typical shear rate regions of different physical processes have been marked on the figure with arrows
Figure 6:
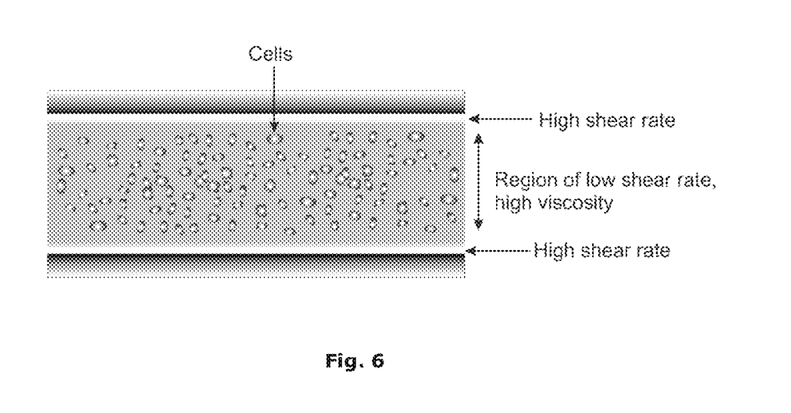
FIG. 6 depicts schematic presentation of a fibril hydrogel containing particles (cells) flowing in a needle. High shear rate region (low viscosity) is located at the gel-needle interface and low shear rate region (very high viscosity) is located in the middle of the needle.

Microbial culture (*Bacillus cereus*) supplemented with 1.5 wt % of native fibril cellulose (total volume 11 ml, containing 1 ml of growth medium) was mixed with PCR lysis buffer and glass beads. The culture was beaten thoroughly, after which phenol-chloroform was added to mixture and centrifuged to form phase separation. The result of centrifugation is shown in FIG. 1. The top layer is aqueous layer containing the desired DNA. The next white narrow phase is the interphase that typically contains amphiphilic molecules, such as denatured proteins and various lipids. The organic phase lies under the interphase and also contains the pelleted glass beads and other precipitated debris. From FIG. 1 it is evident that fibril cellulose is able to form very sharp and easily visible white interphase layer. This layer helps to withdraw, simply by decanting or pipetting the aqueous phase from the top of the organic phase. Moreover, it also prevents the contamination of aqueous phase with the interphase material and with the residual organic phase material, which easily contaminates the aqueous phase when worked with small volumes. The arrow in FIG. 1 points the interphase where fibril cellulose creates clear and visible layer. The layer locks two phases and prevents their mixing during the extraction process.

Example 2. Enumeration of Microorganisms from Fibril Cellulose Carrier

*Bacillus cereus* bacterium was cultivated in two different media, one containing 1.5 wt % of native fibril cellulose and one without it, and it was measured if fibril cellulose has effect on sensitivity on PCR assay.

The growth medium used in the experiment was standard trypsin soy broth, and it was prepared according the manufacturer's instructions and autoclaved for sterility. Before autoclaving the growth medium was divided into the two parts, one of which 1.5 wt % of fibril cellulose was added. Small inoculum of *B. cereus* was grown overnight at 37° C. to reach dense microbial culture, and that was used to inoculate both growth media, about thousand fold dilution was used in the inoculation. Both test media were sampled 0 and 24 hours after the inoculation. 0.1 ml sample of culture was used for PCR based microbial enumeration. The enumeration method was based on the Ruminolyze protocol where the microbial sample is first diluted to washing buffer, and microbial cells are pelleted by centrifugation (10 min 18 000×g). The supernatant was discarded and pellet was suspended to enzymatic lysis buffer and thereafter strongly beaten with glass beads in order to both enzymatically and mechanically lyse microbial cells to release their DNA content. The released DNA was purified with phenol-chloroform extraction, then precipitated with ethanol and finally dissolved to the DNA storage buffer. The *B. cereus* enumeration was performed with two *B. cereus* selective DNA primers and Sybergreen I chemistry. The results are shown in FIG. 2, where *B. cereus* cell numbers on growth media (TBS) and fibril cellulose (fc) in the beginning (0 h) and after overnight incubation analyzed by quantitative PCR are shown.

Accordingly *Bacillus cereus* cell numbers on growth media (TSB) and fibril cellulose (fc) in the beginning (0 h) and after overnight incubation were analyzed by quantitative PCR. The experiment indicates that small number of *B. cereus* cells, about $10^5$ cells/ml, can be detected in the presence of fibril cellulose that indicates that fibril cellulose has no effect on the sensitivity of the PCR assay. Furthermore, 24 hour sample gives higher cell numbers than the 0 hour sample. This means that the dynamic range of PCR is not disturbed by the presence of fibril cellulose and the fibril cellulose does not hinder the PCR reaction when is it run at its maximum speed, in other words when there are large amounts of template DNA. FIG. 2 also shows that more cells are counted in the presence of fibril cellulose at both 0 hours and 24 hours sampling points. This suggests that fibril cellulose aids the DNA isolation and provides higher DNA yields for *B. cereus* enumerations. This suggests that fibril cellulose even improves PCR protocols.

Similar experiments were also performed with other bacterial species, *Clostridium perfringens, Lactobacillus salivarius* and *Desulfovibrio desulficans*. The results were similar to *B. cereus* findings, and they support the contention that the fibril cellulose does not inhibit DNA isolation or PCR procedures.

Example 3. Microbial Quantification in the Presence of Fibril Cellulose

Dilution series (10-, 100 and 1000-fold dilution) of dense *Clostridium perfringens* (Cl. per.) culture (about $10^9$ cells/ml) was prepared in the presence of 1.5 wt % of native fibril cellulose (MFC) and without it. The diluted microbial samples were suspended to lysis buffer and glass beads and exposed to microbial DNA isolation method (as described in example 2 above). After the DNA isolation the DNA samples were used for PCR based enumeration by using *C. perfringens* specific primers and Sybergreen I chemistry. The results of PCR quantification are shown graphically in FIG. 3. The data shows strong linear correlation between PCR results and calculated dilution without any interference from fibril cellulose, i.e. between the dilution and the PCR response in the presence or absence of 1.5 wt % of fibril cellulose.

Example 4. Flow Properties of Fibril Cellulose Hydrogel

The rheological flow properties of fibril cellulose hydrogels show beneficial several features. The hydrogels have a high viscosity at low shear (or rest) for optimum suspending capacity of particles but also show shear-thinning behavior at higher shear rates to enable easy dispensing and injection. The ability of fibril cellulose to provide these kinds of rheological properties was demonstrated in a test series where the viscosity of fibril cellulose dispersions was measured over a broad shear stress (rate) range in a rotational rheometer (AR-G2, TA Instruments, UK).

Fibril cellulose dispersions (hydrogels) show much higher zero-shear viscosities (the region of constant viscosity at small shear stresses) than other water soluble polymers, as shown in FIG. 4. The zero-shear viscosity of fibril cellulose is greatly increased by smaller fibril diameter induced by preceding chemical pretreatment of the starting material. The stress at which shear-thinning behavior starts ("yield stress") is also considerably high for the fibril cellulose dispersions. The suspending ability of a material is the better the higher the yield stress. The particles are effectively stabilized against sedimentation by the combined effects of high zero-shear viscosity and high yield stress and high storage modulus. The gravitational force applied by the particles is much weaker than the yield stress.

In FIG. 5 the viscosity is presented as a function of the measured shear rate. From this figure it is obvious that the viscosity of the fibril cellulose dispersions drops at relatively small shear rates and reaches a similar level as that measured for the reference materials at shear rates of about 200 s-1.

The network structure of fibril cellulose breaks down upon shearing (FIG. 5). Upon the application of a certain stress, the viscosity of the system drops dramatically and a transition from solid-like to liquid-like behavior occurs.

When two-phase liquids, such as flocculated fibril cellulose dispersions, are sheared (e.g. in a rheometer or in a tube), the dispersed phase tends to move away from the solid boundaries, which leads to the creation of a lower-viscosity layer of liquid at the walls of the container (FIG. 6). This phenomenon means that the resistance to flow, i.e. the viscosity is lower at the boundaries than in the bulk of the dispersion. Respectively, pumping, or injection of the fibril cellulose hydrogel with a syringe and a needle or with pipette is easy even at high concentrations (1-4%). The phenomenon enables also easy dispensing of suspensions with minimum disturbance of the particles (cells in the figure).

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

The invention claimed is:

1. A method for the separation of phases, said method comprising:

incorporating a separation agent comprising nanofibrillar cellulose into a mixture;

forming more than one phase from the mixture and separation agent, the more than one phase including a first liquid phase and at least one second phase, the at least one second phase including a second liquid phase immiscible in the first liquid phase, a solid phase, or a semisolid phase;

removing the first liquid phase from the at least one second phase, wherein the separation agent comprises from 0.1 to 20 wt % of nanofibrillar cellulose in an aqueous dispersion, the separation agent forming a barrier or interphase comprising a gel between the first phase and the at least one second phase.

2. The method according to claim 1, wherein the nanofibrillar cellulose is plant derived cellulose or microbial derived cellulose or any combination thereof.

3. The method according to claim 1, wherein the nanofibrillar cellulose is native or chemically modified nanofibrillar cellulose.

4. The method according to claim 3, wherein the nanofibrillar cellulose is ion exchanged nanofibrillar cellulose.

5. The method according to claim 1, wherein the first liquid phase comprises an aqueous phase, optionally comprising at least one polar solvent.

6. The method according to claim 1, wherein the forming more than one phase comprises one or more steps selected from agitation, centrifuging, and settling.

7. The method according to claim 1, wherein the removing the first liquid phase from the at least one second phase comprises one or more steps selected from decanting, pipetting, draining and pumping.

* * * * *